United States Patent [19]

Stern

[11] Patent Number: 5,902,940
[45] Date of Patent: May 11, 1999

[54] DISPOSABLE FLUID SAMPLING APPARATUS OR BAILER

[75] Inventor: Jay Leabman Stern, Los Angeles, Calif.

[73] Assignee: Applied Biogenics, Inc., Bell Gardens, Calif.

[21] Appl. No.: 08/928,215

[22] Filed: Sep. 12, 1997

[51] Int. Cl.$^6$ .................................................. G01N 1/12
[52] U.S. Cl. ...................................... 73/864.63; 294/68.22
[58] Field of Search .......................... 73/863.63, 863.66, 73/863.23; 294/68.22

[56] References Cited

U.S. PATENT DOCUMENTS

| Re. 34,754 | 10/1994 | Dickinson et al. | 166/64 |
|---|---|---|---|
| 3,994,522 | 11/1976 | Hinshaw | 294/68.22 |
| 4,606,233 | 8/1986 | Burney | 73/864.63 |
| 5,404,949 | 4/1995 | Voss | 166/264 |
| 5,421,631 | 6/1995 | Murray | 294/68.22 |
| 5,454,275 | 10/1995 | Kabis | 73/864.51 |
| 5,507,194 | 4/1996 | Scavusso et al. | 73/864 |
| 5,560,429 | 10/1996 | Needham | 294/68.22 |
| 5,597,966 | 1/1997 | Timmons | 73/864.63 |

Primary Examiner—Hezron Williams
Assistant Examiner—Chad Soliz
Attorney, Agent, or Firm—Brown, Martin, Haller & McClain

[57] ABSTRACT

A improved disposable bailer which is made of a pliant or flexible transparent tubing material for the collection of fluids and/or gases. The present invention allows sampling in minimally sized bores or wells which are not perfectly straight. Also, the invention permits sampling at the top of a fluid column or within a fluid column and permits acquisition of a vapor sample on top of the fluid column. In this embodiment, a vapor or liquid specimen may be sampled through a septum on the surface of the bailer. Also in this embodiment, fluids and gases may be collected through a flexible nozzle which acts as a valve when the collected sample constricts the nozzle opening due to the presence of the collected sample in the tubing. In another embodiment, samples are collected through the top of the tubing, allowing selective sampling within a column of fluid when the tubing is immersed. Another embodiment utilizes both the flexible nozzle and top opening to collect samples. Perforated strips applied across either or both ends, breakage of which is preferably necessary for use, indicate usage or tampering.

17 Claims, 3 Drawing Sheets

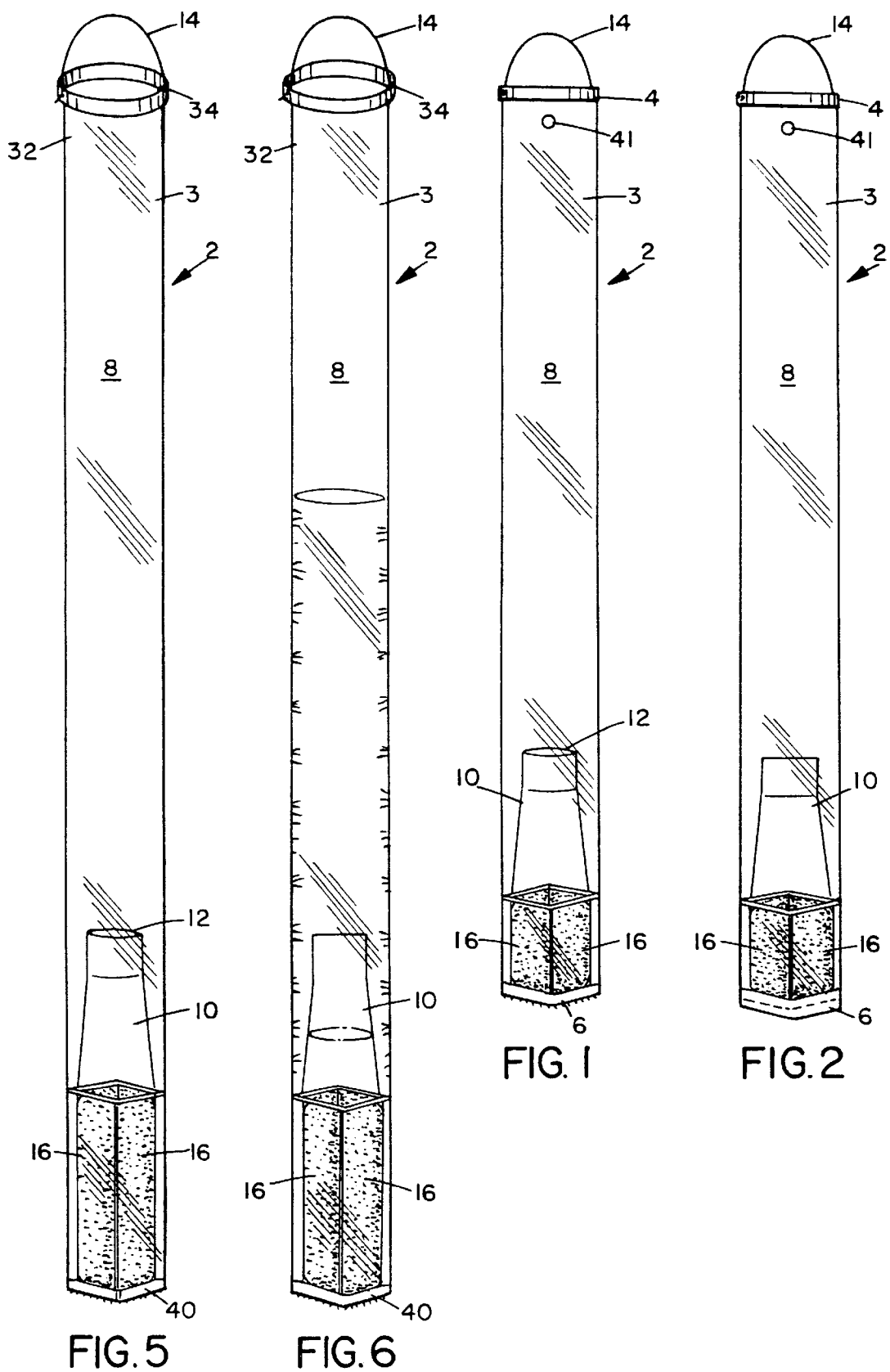

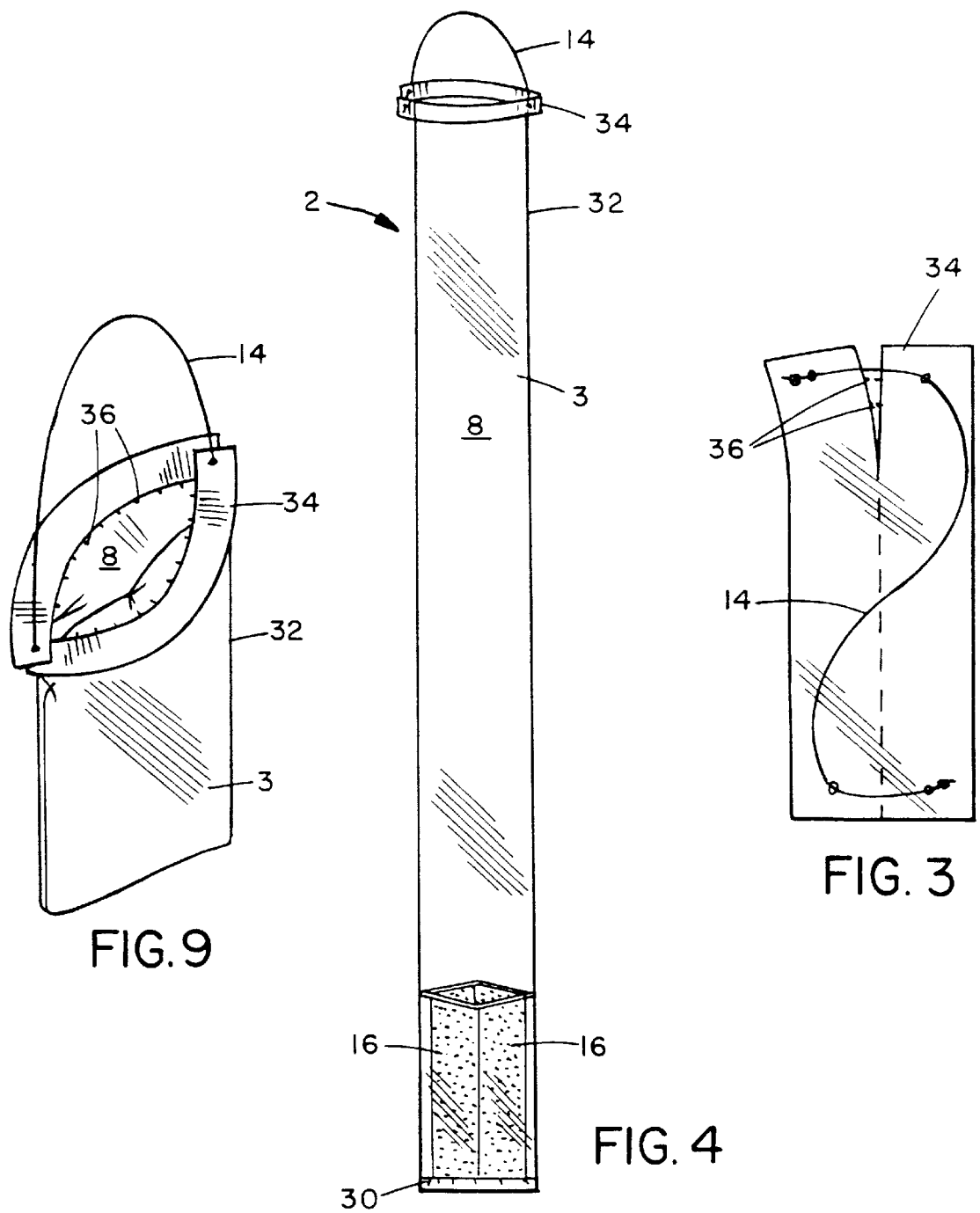

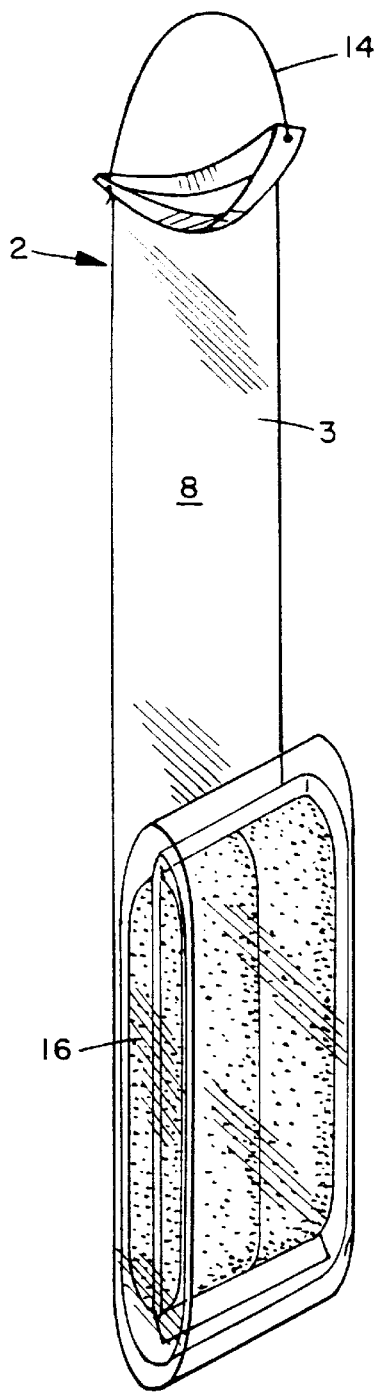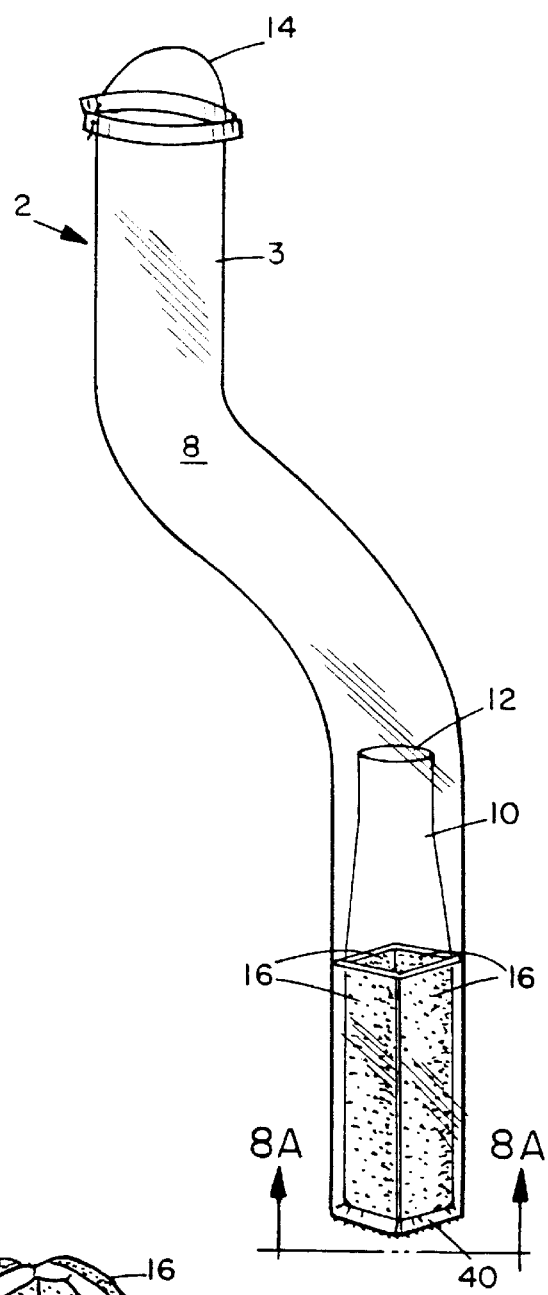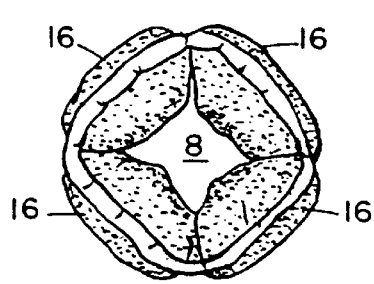
FIG. 7
FIG. 8
FIG. 8A

DISPOSABLE FLUID SAMPLING APPARATUS OR BAILER

The field of the invention is disposable sampling devices. Sampling apparatus or bailers are intended to be used to recover specimens of water for scientific, engineering or quality assurance purposes. In some cases, bailers are used to remove water from a ground water well. Such bailers are generally buckets or long cylindrical tubes of a durable material such as steel or heavy plastic and are generally designed to be nondisposable.

Bailers used to recover specimens of water for scientific, engineering or quality assurance purposes are either disposable or nondisposable. Nondisposable bailers are similar or identical to those used for removal of water. When identical, they are the same bailer. When similar, they are of a more delicate or diminutive construction.

Conventional disposable bailers generally consist of thin, stiff or rigid cylindrical plastic cases typically two to three feet in length with a top mouth and bottom opening. Many conventional disposable bailers are equipped with stainless steel weights to overcome the buoyancy of the plastic from which the bailer is fabricated. The bottom opening is equipped with a ball or diaphragm valve, either of which must seat securely to prevent leakage.

Virtually any sediment entering conventional, disposable bailers along with the water being sampled defeats the precision nature of the seat, permitting profuse leakage of water as the sample is hauled to the surface of the well. For example, a three-foot long bailer can nominally contain about 1,800 cubic centimeters (cc) of liquid. When brought to the surface of even a 30-foot deep well, it is not uncommon for less than 100 cc of liquid to remain. In fact, to compensate for leakage, conventional disposable bailers are made longer than they otherwise need to be. If not transferred to a specimen container immediately, even this small volume may be lost necessitating multiple transits of the well by the bailer to retrieve a sufficient sample.

The repeated raising and lowering of the bailer can and frequently will perturb the ground water conditions and any constituents thereof, disrupting its equilibrium with any vapor on top of the ground water. Consequently, the contents of the first and final bailer volumes, gathered over an extended time period, are likely to be substantially different from each other. This leads to inaccuracies in data quantification.

Disposable bailers are intended for a single use. However, conventional, disposable bailers are poorly suited for this purpose. They are expensive, sometimes prompting covert reuse from body of water to body of water for economical reasons. Reuse allows undesirable carry-over of contaminants from one water sample to another. Further, storage of conventional, disposable bailers commits significant storage space, thus encouraging field workers to minimize on the number of bailers which they otherwise would carry for sampling purposes. One dozen, typical three-foot long bailers requires at least 1,750 cubic inches of space.

Conventional, disposable bailers are also awkward to use. They crush easily or split unless carefully handled. Importantly, if a well bore is not perfectly straight, conventional bailers may not descend to the base of the bore, becoming lodged at the point where the bore changes direction. For this reason, conventional, disposable bailers are not recommended for sampling water bodies through well bores much less than four inches in diameter.

Stainless steel weights, often as rings around the plastic shell, have been incorporated into various conventional, disposable bailers. While stainless steel is less reactive than other metals, and is probably not a concern where organic constituents in ground water is being investigated, the stainless steel can react with salts or in acidic waters. This will alter the composition of the sample being retrieved and could invalidate it.

Conventional, disposable bailers are also unable to adequately gather samples from bodies of water at least as deep as they are tall. In such cases, material floating on the surface of the water is necessarily not collected in a concentration characteristic of its in situ condition because water enters the sampling device from the bottom only. Moreover, conventional, disposable bailers are necessarily made of opaque or translucent material thereby preventing the user from assessing the condition of the sample prior to transfer of its contents.

The present invention solves the problems inherent in the conventional, disposable bailers. The present invention does not leak, or presents minimal leakage in use. Thus, one transit of the well is generally sufficient to gather ample liquid for testing. Because just one transit is needed, the collected sample is more closely representative of the water body being sampled than if it had been obtained with a conventional, disposable bailer.

The present invention is of a compact design. In storage, a dozen will occupy only about 72 cubic inches. It uses no precision parts and is free of all metals which may alter sample composition. It is much less costly than conventional disposable bailers thereby encouraging a single use.

The present invention may be two-thirds the length of conventional disposable bailers because of its greater efficiency in collecting and containing samples. It is tolerant of close-fitting well bores and bends to accommodate less than straight wells. The invention is typically transparent to allow inspection of the sample prior to transfer to other containers. Further, the present invention may be provided in at least three different variants to permit sampling at the top of, or within, a column of water and to permit acquisition of a vapor sample on top of the water column, should such be desired.

Thus, it is an object of the present invention to provide fluid sampling apparatus that overcome the problems with conventional bailers and permit retrieval or sampling of water and fluids on top of water, especially ground water in wells, monitoring wells or holes bored to ground water. An object of the present invention is to provide a fluid sampling apparatus to permit retrieval or sampling of surface water where devices such as cups or other containers are unsuitable. An object of the present invention is to provide an apparatus that allows sampling of the aforementioned fluids with a disposable device. Another object is to permit such sampling at more economical or modest price coupled with greater efficiency than conventional bailers. Other and further objects will appear to those skilled in the art from the specification and drawings, whereby FIG. 1 is an elevation view illustrating one embodiment of the invention with a tubing having a sealed first end and an open nozzle to allow samples to be collected through an open second end.

FIG. 2 is also an elevation view of the embodiment shown in FIG. 1 showing the nozzle closed and with a perforated polyethylene strip, breakage of which is preferably necessary to permit use.

FIG. 3 is a plan view illustrating a perforated polyethylene strip applied to either or both ends of the bailer, the breakage of which is preferably necessary to permit sample collection. The embodiment shown in FIG. 3 is preferably intended for attachment to the first end.

FIG. 4 is an elevation view illustrating one embodiment of the invention with the bottom sealed and a perforated polyethylene strip at the top.

FIG. 5 is an elevation view illustrating another embodiment with perforated polyethylene strips at the top or first end and bottom or second end, and the inlet nozzle in the open position.

FIG. 6 is another elevation view of the embodiment shown in FIG. 5, containing water, to illustrate how the nozzle collapses, effecting a seal, when fluid rests on top of it.

FIG. 7 is a perspective view showing one preferred technique for storing an embodiment of the invention and illustrating the flexibility of the pliant tubing.

FIG. 8 is an elevation view further illustrating the flexibility of the preferred pliant tubing and its ability to snake around crooked openings.

FIG. 8a is another view of an embodiment of the invention taken along line 8a—8a in FIG. 8.

FIG. 9 is a detailed view of the top perforated polyethylene strip with its perforation open for use.

Referring to the Figures, FIGS. 1 and 2 show an embodiment of the improve bailer 2. In this embodiment, the bailer 2 is preferably constructed of flat-lay polyethylene tubing 3 having a thickness of approximately four mils, with a "mil" equal to one-thousandth of an inch. The use of polyethylene is preferable because it is transparent allowing visual inspection of a collected sample as well as being inert toward collected samples. The first end 4 of the tubing 3 is sealed and the second end 6 is open.

Within the tubing 3 is an internal cavity 8 for the collection of fluids or gases or both. Fluids and/or gases enter the open second end 6 through a nozzle 10 which is also formed of flat-lay polyethylene approximately four mils thick and securely welded to tubing 3. The nozzle 10 is preferably funnel-shaped along a portion of its length and terminates in an inlet port 12 within the internal cavity 8 at a distance of approximately six inches from the second end 6, although other configurations are possible. The inlet port 12 is shown in an open configuration in FIG. 1. The inlet port 12 preferably has a diameter of approximately one inch.

The bailer 2 is deployed flat along its internal cavity 8 length, in a fluid body such as a well. A retrieval line 14 is secured to the first end 4 as shown in FIGS. 1 and 2 and is used to deploy the bailer 2. The natural buoyancy of the tubing 3 is counterbalanced by inexpensive, inert ballast, in this case silica sand which has been washed and roasted to eliminate any organic contaminants or soluble salts. The ballast is contained within chambered compartments 16 formed between the tubing 3 and part of the nozzle 10. It is positioned at the second end 6 as shown in the Figures. In this embodiment, there are preferably four compartments 16 each containing about 0.75 ounces of sand.

In one embodiment of the invention, when the open second end 6 contacts the top of the liquid in a well or other body, air is trapped in the nozzle 10 and forced to enter the internal cavity 8 by the force of gravity acting on the bailer 2. The trapped air rises through the internal cavity 8, partially inflating the tubing 3 and reducing the effective pressure at the second end 6. This permits water or fluid on the water to enter the cavity 8 through the inlet port 12. The tubing 3 may preferably be cycled up and down immediately above and into the body of water sampled to maximize both the yield of liquid sample as well as vapor and gas existing at the interface of the water or fluid on top of the water. However, cycling is not mandatory unless maximum water yield is desired. More liquid and gas will enter the bailer 2 through the second end 6 with each cycle until the tubing 3 contains about half liquid and half gas. The tubing 3 becomes cylindrical and is turgid at this point, preventing entry of more liquid or gas. Back flow through the inlet port 12 is prevented by collapse of the nozzle 10 due to pressure of the fluid now on top of the nozzle 10.

Further, gas sampling can be conducted by puncturing the tubing 3 above the level of the collected liquid with a sampling needle and syringe or similar apparatus. A self-sealing septum 41 may preferably be included with the bailer 2 by applying a small bead of silicone rubber to the tubing 3 anywhere above its mid-point as shown in FIGS. 1 and 2. Gas sampling is then conducted through the septum 41 by a sampling needle. By inverting the bailer 3, liquid will flow to its first end 4, where it may be sampled through the septum 41 as well.

Preferably, the diameter of the turgid tubing 3 is one to three inches, although other diameters are within the scope of the invention. When other diameter tubing is employed, the dimension of the nozzle 10 is changed to assure Reynolds number consistency.

FIGS. 3 and 4 illustrate another embodiment with a sealed bottom 30 and a top 32 having a polyethylene strip 34 having a series of perforations 36. There is no nozzle 10 in this embodiment as fluid samples are collected via the top 32 after the strip 34 is "broken" by preferably tearing the strip 34 along the perforations 36. This is shown in FIG. 4. An advantage of the perforations 36 is that they provide positive evidence of prior use or tampering by a simple visual inspection.

This embodiment can be used to gather specimens from within a column of fluid. As shown in FIGS. 3 and 4, this embodiment has a semi-rigid polyethylene strip 34 securely welded to the top 32 of the tubing 3. This strip 34 is approximately the same length as the width of the tubing 3 as illustrated in FIG. 4, and is approximately one-inch wide.

When deployed, the strip 34 is perforated along the long axis of the strip 34 as shown in FIG. 3 providing an opening to the internal cavity 8 as shown in detail in FIG. 9. In this embodiment, there are preferably four chambered compartments 16 arranged as shown in FIG. 4 each containing about 0.75 ounces of sand to compensate for buoyancy forces on the tubing 3.

When the tubing 3 is deployed to collect a sample from a fluid body, hydrostatic forces on the sides of the tubing 3 prevent the top 32 of the tubing 3 from opening while it is lowered into a body of fluid and then immersed in the fluid body. Then, slight upward movement of the tubing 3 via the retrieval line 14 allows the immersing fluid to funnel into the tubing 3 through the top 32. As cycles of slight upward movement followed by downward movement are repeated, more and more fluid enters the tubing 3 through the top 32 until the tubing 3 is approximately two-thirds full by volume, but substantially completely full along the height of the tubing 3.

As the tubing 3 is withdrawn from the fluid body, the collected fluid flows downward in response to gravitational forces, producing a void above the collected fluid in the internal cavity 8. Further, when it is withdrawn completely, the tubing 3 assumes a cylindrical shape in that portion occupied by water with that portion of the tubing 3 above the collected water partially collapsing to form a seal which excludes atmospheric air.

FIGS. 5 and 6 illustrate another embodiment of the invention which has a combination of initially sealed top 32 and bottom 40 openings, each sealed with a strip 34, and a nozzle 10. This allows filling of the tubing 3 by both the top 32 and bottom 40 after the strips 34 are broken as described above. This also allows filling of the tubing 3 by the bottom opening 40 through the nozzle 10 as previously described. This combination is shown in FIG. 6. In this embodiment, there are preferably four chambered compartments 16 each containing about 0.75 ounces of sand to act as ballast and the nozzle 10 extends into the internal cavity a distance of approximately 3 inches. This embodiment is capable of collecting a fluid sample of less height than the length of the tubing 3.

The use of a pliant material such as flat-lay polyethylene tubing permits storage of the bailers in a limited storage space in a rolled-up configuration as illustrated in FIG. 7. The present invention also permits the sampling of fluid in minimally sized bores or wells which are not perfectly straight as illustrated in FIG. 8. An end view showing a preferred arrangement of the compartments 16 and a preferred cylindrical configuration is shown in FIG. 8a. The present invention is not limited to the use of polyethylene, but includes other suitable inert and easily fabricated materials such as paper stock coated with a waterproof film and homogeneous or heterogeneous membranes including supported Teflon® film.

While embodiments of the present invention and modifications thereto have been shown and disclosed in the drawings and specification, alternate embodiments of the present invention may be apparent to a person of ordinary skill in the art and this application is intended to include those embodiments within the full breadth and scope of the claims. The present invention is not limited by any parameters described herein and the present invention need not include all of the features disclosed in the single embodiment, but rather one or more features may be included.

What is claimed is:

1. An improved bailer comprising:
    a pliant tubing having a sealed first end and a second end and defining an expandable, interior cavity;
    buoyancy-compensating ballast compartments secured to said pliant tubing; and
    an inlet nozzle secured adjacent to said second end and extending into said interior cavity, said inlet nozzle formed of a unitary, pliant material and adapted to permit inflow of fluid and gases into said pliant tubing and reversibly constrict outflow of collected fluid and gases by flattening of said inlet nozzle solely due to gravity acting upon said collected fluids and gases within said interior cavity.

2. The improved bailer of claim 1 wherein said pliant tubing and said pliant material are comprised of flat-lay polyethylene tubing.

3. The improved bailer of claim 1 wherein a septum of self-sealing polymeric material is placed upon the exterior of said pliant tubing to enable access to contents of said pliant tubing by syringe.

4. The improved bailer of claim 1 wherein said second end may be sealed with a perforated strip, the breakage of which indicates use or tampering.

5. The improved bailer of claim 1 wherein said ballast compartments comprise one or more enclosed chambers secured adjacent to said second end.

6. The improved bailer of claim 5 wherein said ballast compartments contain an inert material.

7. An improved disposable bailer for the collection of fluids and gases, said bailer comprising a flexible tubing having a first end, a second end and ballast compartments secured adjacent to said second end to compensate for buoyancy effects during collection of said fluids and gases, said bailer comprising:
    one-piece valve means for funneling fluids and gases into said flexible tubing through a flexible nozzle and inhibiting the outflow of fluids or gases collected within said flexible tubing by flattening of said nozzle solely by force of gravity acting upon one or more of said collected fluids or gases.

8. The improved disposable bailer of claim 7 wherein said flexible tubing and said flexible nozzle are comprised of polyethylene.

9. The improved disposable bailer of claim 7 wherein said first and second ends are comprised of perforated polyethylene strips, the breakage of which indicates use or tampering.

10. The improved disposable bailer of claim 7 wherein said ballast compartments comprise one or more enclosed chambers containing an inert material.

11. The improved disposable bailer of claim 10 wherein said inert material is sand.

12. An improved bailer comprising:
    a pliant tubing having an open top and a bottom and having an expandable, interior cavity, said bottom being sealed;
    one or more buoyancy compensating ballast compartments secured adjacent to said bottom; and
    perforated strip means, secured to the top of said pliant tubing, breakage of which permits inflow of fluids into said cavity through said top when said tubing is immersed in a fluid body.

13. The improved bailer of claim 12 wherein fluid inflow into said cavity through said top due to external pressure from said immersing fluid body occurs when said tubing is drawn upward through said immersing fluid body.

14. The improved bailer of claim 12 wherein said pliant tubing is comprised of flat-lay polyethylene tubing.

15. The improved bailer of claim 12 wherein said ballast compartments comprise enclosed chambers containing an inert material.

16. The improved bailer of claim 15 wherein said inert material is sand.

17. The improved bailer of claim 12 wherein breakage of the perforated strip indicates use or tampering.

* * * * *